United States Patent [19]

Iggulden et al.

[11] Patent Number: 4,893,729

[45] Date of Patent: Jan. 16, 1990

[54] SELECTABLE MIXING BOTTLE

[75] Inventors: Jerry R. Iggulden, 21600 Cleardale St., Newhall, Calif. 91321; Donald A. Streck, 832 Country Dr., Ojai, Calif. 93023

[73] Assignees: Jerry R. Iggulden, Santa Clarita; Donald A. Streck, Ojai, both of Calif. ; a part interest to each

[21] Appl. No.: 216,289

[22] Filed: Jul. 8, 1988

[51] Int. Cl.⁴ .............................................. B67D 5/22
[52] U.S. Cl. ...................................... 222/42; 222/48; 222/134; 222/145; 222/94; 222/212
[58] Field of Search .................... 222/94, 144, 145, 48, 222/42, 142.9, 142.5, 134, 212

[56] References Cited

U.S. PATENT DOCUMENTS

| | | | |
|---|---|---|---|
| 2,592,279 | 4/1952 | Heier | 222/48 |
| 2,830,730 | 4/1958 | Saffir | 222/94 |
| 2,944,704 | 7/1960 | Taylor | 222/94 |
| 2,944,705 | 7/1960 | Strumot | 222/94 |
| 3,335,912 | 8/1967 | Reeves | 222/94 |
| 4,271,984 | 6/1981 | Ductos et al. | 222/144.5 |
| 4,585,149 | 4/1986 | Zulauf | 222/144.5 |
| 4,771,919 | 9/1988 | Ernst | 222/94 |

FOREIGN PATENT DOCUMENTS 1138690  1/1969  United Kingdom ............. 222/144.5

Primary Examiner—H. Grant Skaggs
Attorney, Agent, or Firm—Donald A. Streck

[57] ABSTRACT

A bottle for holding, mixing, and dispensing an adjustable SPF mixture of a lotion and a liquid containing a sunscreening agent. There is a plastic bottle containing first and second compartments for containing, respectively, the lotion and the sunscreen agent-containing liquid and having a cylindrical neck at the top thereof containing a first bore therethrough communicating with the first compartment and a second bore therethrough communicating with the second compartment. The first bore is concentrically disposed in the neck and sized for passing known quantities of the lotion with the second bore being peripherally disposed with respect to the first bore and sized to add a quantity of the sunscreen agent which will impart a pre-selected maximum SPF value to dispensed quantities of mixtures of the lotion and the sunscreen agent. A selector dial is rotatably mounted on the neck, having a central cap portion covering the neck, a central bore through a top member thereof concentrically disposed over the first bore, and a plurality of various diameter metering bores disposed peripherally through the top member concentrically disposed to pass over the second bore as the selector dial is rotated on the neck with indicia disposed for indicating the SPF value of the metering bores. A mixing chamber member is disposed over the central cap portion and has an internal mixing chamber communicating with the first and second bores and the central and metering bores on a bottom end thereof and a third bore therethrough at a top end thereof for the egress of the mixed lotion and sunscreen agent-containing liquid.

5 Claims, 2 Drawing Sheets

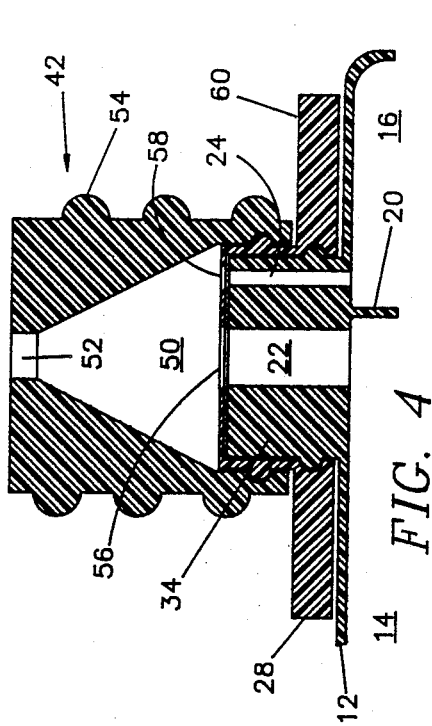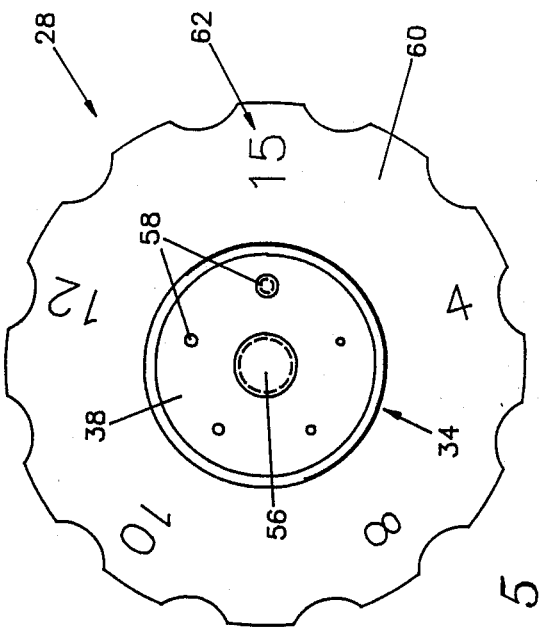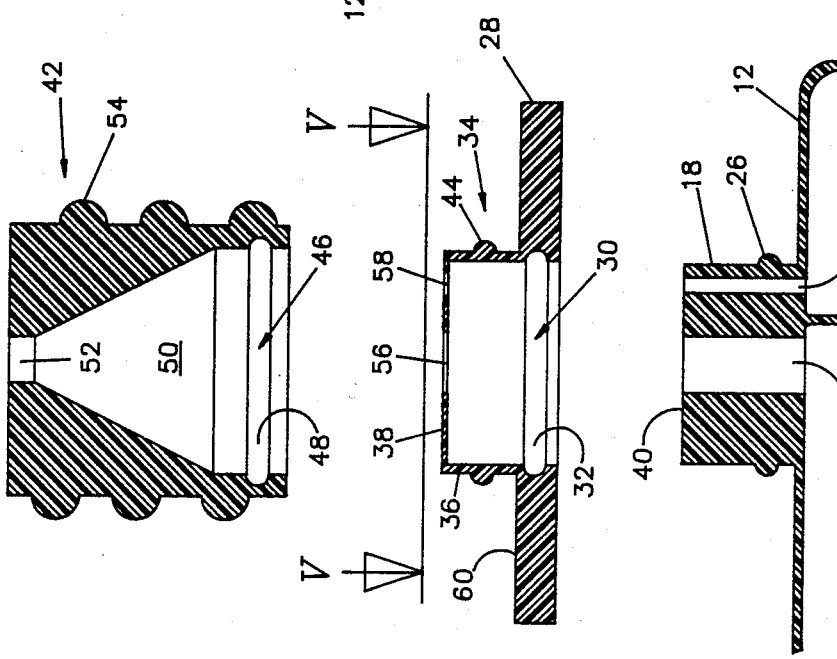

SELECTABLE MIXING BOTTLE

BACKGROUND OF THE INVENTION

The present invention relates to plastic bottles and, more particularly, to a bottle for holding, mixing, and dispensing a mixture of two liquid components comprising, a plastic bottle having two compartments for containing respective ones of the two liquid components and having a cylindrical neck at the top thereof containing a first bore therethrough communicating with one of the compartments and a second bore therethrough communicating with the other of the compartments; and, a generally cylindrical mixing chamber member disposed over the neck, the mixing chamber member having an internal mixing chamber communicating with the first and second bores on a bottom end thereof and having a third bore therethrough at a top end thereof for the egress of the two liquid components following their being squeezed from the two compartments through the first and second bores into the mixing chamber, the mixing chamber member further having threads formed on an outer surface thereof for removably receiving an internally threaded cap.

Scientists are emphasizing more and more that people who venture out into the sun have to worry about protection from ultraviolet (UV) radiation to prevent premature aging of the skin from damage to the skin's connective tissue and minimize the cancer-producing effects of the ultraviolet radiation. The results of recent research indicates that while the longer-wavelength ultraviolet A (UVA) rays (i.e. the "tanning" rays) have long been thought to be innocuous, they may, in fact, cooperate with the shorter-wavelength ultraviolet B (UVB) rays in causing skin damage.

While, for a long time, the only solution to the problem was avoidance of the sun's rays by staying out of the sun or covering the body against exposure to the rays, recently, effective sunscreen agents have been made available for topical application to the skin. Prior so-called "suntanning" oils and lotions did little more than provide a lubricating effect to the skin to avoid dryness. By adding derivatives of PABA (para-aminobenzoic acid) for example, however, the products can be made to block the UVB rays. Likewise, by adding, for example, benzone compounds (such as benzophenone or oxybenzone), the UVA rays can be blocked. An improved sunscreen additive called Photoplex containing Parsol 1789 (butyl methoxydibenzoylmethane) has been used effectively in Europe for years and is soon to be approved by the FDA for use in the United States.

While this is all very well and good, it creates problems for the typical family going to the beach, for example. The sunscreening lotions come in a variety of sunscreening capabilities designated by a "SPF" number with the smaller numbers indicating very little screening of the sun's UV rays and the larger numbers indicating the screening out of a large percentage of the sun's UV rays. Thus, in protecting the entire family throughout the day, a parent must have a supply of lotions with varying SPF numbers. The baby must have SPF 15 throughout the day because of the tender nature of a baby's skin. Other children tend to tan quickly and, therefore, require SPF 8 for most of the day. Mother, who is "working" on her tan wants to start out with SPF 2 and progressively move up to SPF 15 by late in the day. Father, who is tan on his neck and arms and unexposed on the rest of his body, wants SPF 2 on the tan areas and at least SPF 8 on the unexposed areas as he tends to burn easily. The result is depicted in FIG. 1. The family must take multiple standard bottles 10 of lotion each containing lotion with a different SPF number, as indicated.

Wherefore, it is the object of the present invention to provide a bottle for holding and dispensing liquids with variable qualities and including the capability of selectively mixing ingredients during dispensing so that the qualities are adjustably selectable by the user.

It is another object of the present invention to provide a bottle for containing and dispensing a lotion employed during exposure to the sun in one compartment and an active ingredient for preventing the passage of ultraviolet rays therethrough in another compartment wherein the amount of the active ingredient added to the lotion during dispensing is selectably variable.

It is still another object of the present invention to provide a bottle that will hold and dispense a lotion employed during exposure to the sun with selectable SPF values.

Other objects and benefits of the present invention will become apparent from the description contained hereinafter when taken in conjunction with the drawing figures which accompany it.

SUMMARY

The foregoing objects have been achieved in a bottle for holding, mixing, and dispensing an adjustable mixture of a lotion and a liquid containing an active ingredient comprising, a plastic bottle containing first and second compartments for containing, respectively, the lotion and the active ingredient-containing liquid and having a cylindrical neck at the top thereof containing a first bore therethrough communicating with the first compartment and a second bore therethrough communicating with the second compartment, the first bore being sized for passing known quantities of the lotion and the second bore being sized in relation to the first bore so as to add a quantity of the active ingredient which will impart a pre-selected quality to dispensed quantities of mixtures of the lotion and the active ingredient; a generally cylindrical mixing chamber member disposed over the neck, the mixing chamber member having an internal mixing chamber communicating with the first and second bores on a bottom end thereof and having a third bore therethrough at a top end thereof for the egress of the lotion and the active ingredient-containing liquid following their being squeezed from the first and second compartments through the first and second bores into the mixing chamber; the mixing chamber member further having threads formed on an outer surface thereof for removably receiving an internally threaded cap; and, means for adjusting the size of the second bore whereby the quantity of the active ingredient and thereby the quality of dispensed quantities of mixtures of the lotion and the active ingredient are adjustable.

In the preferred embodiment, indicia means are associated with the means for adjusting the size of the second bore for indicating the quality of a mixture associated with sizes of the second bore whereby the quantity of the active ingredient and thereby the quality of dispensed quantities of mixtures of the lotion and the active ingredient is selectable.

Further in the preferred embodiment, the first bore is concentrically disposed in the neck; the second bore is peripherally disposed with respect to the first bore; and, the means for adjusting the size of the second bore comprises a selector dial rotatably mounted on the neck, the selector dial having a central cap portion covering the neck over which the mixing chamber member is disposed, the central cap portion having a central bore through a top member thereof concentrically disposed over the first bore and a plurality of various diameter metering bores disposed peripherally through the top member concentrically disposed to pass over the second bore as the selector dial is rotated on the neck. Preferably, the indicia means are on the selector dial.

DESCRIPTION OF THE DRAWINGS

FIG. 3 is an enlarged, exploded, cutaway, elevation view of the top of the bottle of FIG. 2.

FIG. 4 is an enlarged, assembled, cutaway, elevation view of the top of the bottle of FIG. 2.

FIG. 5 is a top view of the selector dial of the bottle top of the present invention from the plane V—V of FIG. 3.

DESCRIPTION OF THE PREFERRED EMBODIMENT

Figures 1, 2:
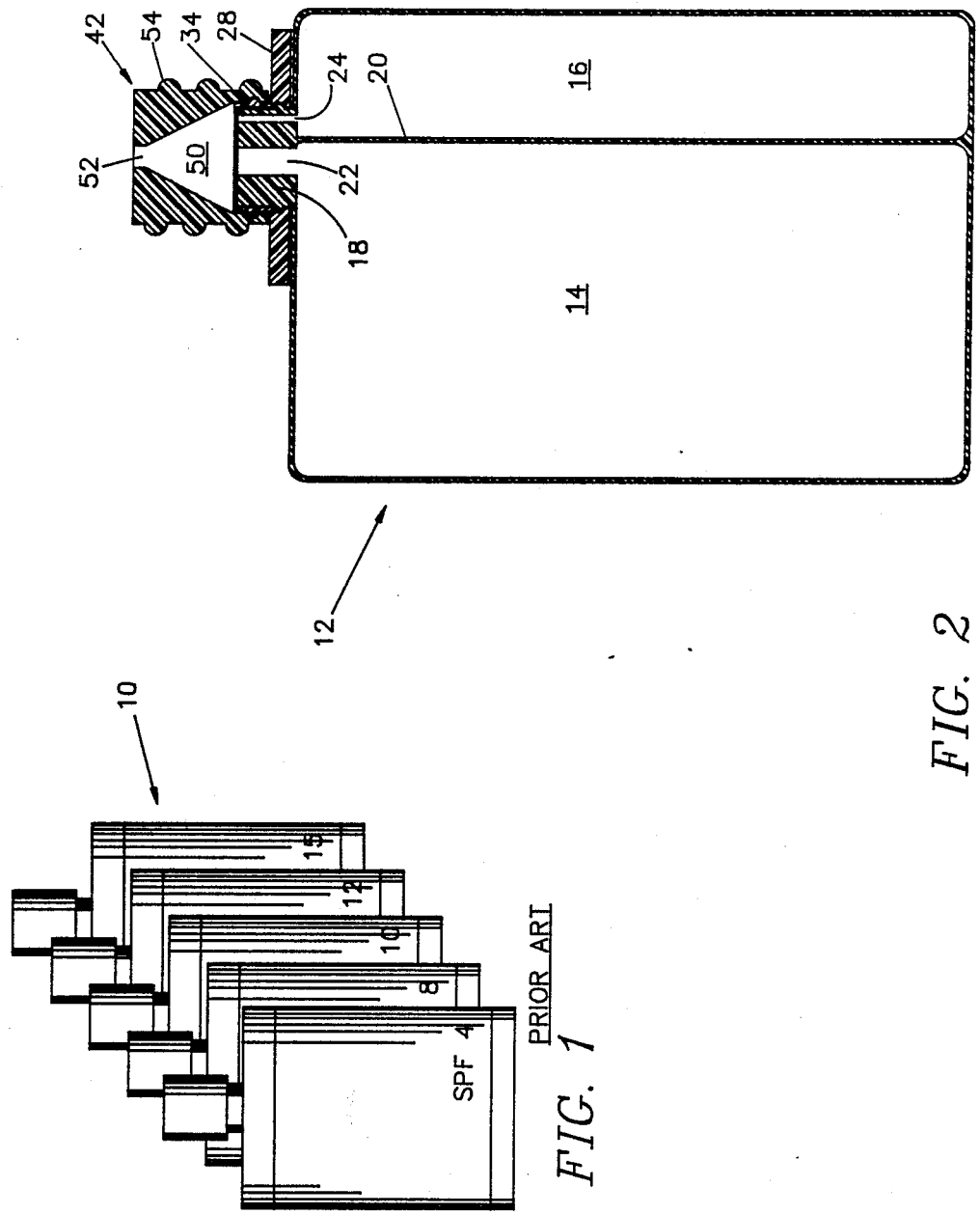
FIG. 1 is a pictorial representation of the prior art solution to the problem solved by the present invention.
FIG. 2 is a cutaway elevation drawing of a bottle according to the present invention.

The bottle of the present invention is shown in FIGS. 2–5. While it is primarily intended for use with sunscreening lotions, those skilled in the art will appreciate that there may be other uses for which it is applicable as well. Thus, will the description and drawings concentrate on the sunscreening lotion application thereof, it is the inventors' intent that the specification and appended claims be accorded a breadth in accordance with the scope and spirit of the invention being disclosed herein.

As shown in FIG. 2 with particularity, the bottle 12 of the present invention is of plastic (so as to be squeezable) and is divided into two compartments 14, 16. Again, while two compartments are shown, those skilled in the art will readily recognize and appreciate that more compartments could be employed, if desired. The larger compartment 14 is intended to contain a lubricating type of skin lotion, or the like. The smaller compartment 16 is intended to contain a sunscreen concentrate in an appropriate liquid vehicle. As best seen in the drawings of FIGS. 3–5, the bottle 12 has a cylindrical neck 18 at the top straddling the internal divider 20 that separates the compartments 14, 16. The neck 18 has a concentric central bore 22 of relatively large diameter therethrough communicating with the large compartment 14. It also has an offset bore 24 of smaller diameter therethrough communicating with the small compartment 16. Additionally, the neck 18 has a circumferential retaining ridge 26 on the outer surface thereof over which a selector dial 28 is rotatably snapped. The selector dial 28 is also preferably of plastic and has a central bore 30 containing a circumferential retaining groove 32 on the inner surface thereof which receives the retaining ridge 26 therein. The selector dial 28 has a central cap portion 34 having cylindrical sidewalls 36 extending upward from the periphery of the bore 30 and a covering top member 38 extending between the sidewalls 36. The sidewalls 36 are of a height such that the top member 38 is tight against the top surface 40 of the neck 18 when the selector dial 28 is snapped onto the neck 18 as shown in FIG. 4.

The selector dial 28 has a circumferential retaining ridge 44 on the outer surface thereof over which a generally cylindrical, plastic, mixing chamber member 42 is snapped. The mixing chamber member 42 has a central bore 46 at the bottom thereof containing a circumferential retaining groove 48 on the inner surface thereof which receives the retaining ridge 44 therein. The mixing chamber member 42 has a tapered, frusto-conical mixing chamber 50 therein communicating with the bore 46 on one end an outlet opening 52 on the other end. The exterior surface of the mixing chamber member 42 has threads 54 formed therein onto which a cap (not shown) can be threaded. The cap can be of the type which is removable for dispensing of the ingredients in the bottle 12 or of the type which has a flip-up/down opening member, as desired.

As best seen in FIG. 5, the selector dial 28 also has a central bore 56 through the top member 38 concentrically disposed over the bore 22. Thus, as the selector dial 28 is rotated on the neck 18, there is a constantly open path through the bores 22, 56 between the large compartment 14 and the mixing chamber 50. Additionally, there are a plurality of metering bores 58 disposed peripherally through the top member 38 concentrically disposed to pass over the bore 24 as the selector dial 28 is rotated on the neck 18. The metering bores 58 are of various diameters. Thus, there is an adjustable path through the bores 24, 58 between the small compartment 16 and the mixing chamber 50. The top surface 60 of the selector dial 28 is provided with indicia 62 correlated to the metering bores 58. That is, adjacent each metering bore 58 there is an indicia 62 indicating the SPF that will result if that particular metering bore 58 is positioned over the bore 24 and the contents of the compartments 14, 16 is squeezed through the bores 22, 24, 56, 58 into the mixing chamber 50 and out the opening 52.

Since the consumption of the sunscreen concentrate will vary with respect to the consumption of the lotion as a function of the SPF values selected and may, in fact, be consumed before the supply of lotion is exhausted, it is preferred and suggested that the lotion be of a fairly neutral color and that the sunscreen concentrate have a detectable coloring added thereto so that its non-presence in the resultant mixture will noted should the supply thereof be exhausted.

Wherefore, having thus described our invention, we claim:

1. A bottle for holding, mixing, and dispensing a mixture of two liquid components comprising:
   (a) a plastic bottle having two compartments for containing respective ones of the two liquid components and having a cylindrical neck at the top thereof containing a first bore therethrough concentrically disposed in said neck and communicating with one of said compartments and a second bore therethrough peripherally disposed with respect to said first bore and communicating with the other of said compartments, one of said two compartments being a chamber for holding a lotion, the other of said two compartments being a chamber for holding an active ingredient for imparting variable qualities to a mixture of said lotion and said active ingredient;

(b) a generally cylindrical mixing chamber member disposed over said neck, said mixing chamber member having an internal mixing chamber communicating with said first and second bores on a bottom end thereof and having a third bore therethrough at a top end thereof for the egress of the two liquid components following their being squeezed from said two compartments through said first and second bores into said mixing chamber, said mixing chamber member further having threads formed on an outer surface thereof for removably receiving an internally threaded cap, said first bore being sized for passing known quantities of said lotion, said second bore being sized in relation to said first bore so as to add a quantity of said active ingredient which will impart a preselected quality to dispensed quantities of mixtures of said lotion and said active ingredient; and additionally, (c) means for adjusting the size of said second bore comprising a selector dial rotatably mounted on said neck, said selector dial having a central cap portion covering said neck over which said mixing chamber member is disposed, said central cap portion having a central bore through a top member thereof concentrically disposed over said first bore and a plurality of various diameter metering bores disposed peripherally through said top member concentrically disposed to pass over said second bore as said selector dial is rotated on said neck whereby the quantity of said active ingredient and thereby the quality of dispensed quantities of mixtures of said lotion and said active ingredient are adjustable.

2. The bottle of claim 1 and additionally comprising: indicia means on said selector dial for indicating the quality of a mixture associated with respective ones of said metering bores whereby the quantity of said active ingredient and thereby the quality of dispensed quantities of mixtures of said lotion and said active ingredient is selectable.

3. A bottle for holding, mixing, and dispensing an adjustable mixture of a lotion and a liquid containing an active ingredient comprising:

(a) a plastic bottle containing first and second compartments for containing, respectively, the lotion and the active ingredient-containing liquid and having a cylindrical neck at the top thereof containing a first bore therethrough communicating with said first compartment and a second bore therethrough communicating with said second compartment, said first bore being sized for passing known quantities of said lotion and said second bore being sized in relation to said first bore so as to add a quantity of said active ingredient which will impart a pre-selected quality to dispensed quantities of mixtures of said lotion and said active ingredient;

(b) a generally cylindrical mixing chamber member disposed over said neck, said mixing chamber member having an internal mixing chamber communicating with said first and second bores on a bottom end thereof and having a third bore therethrough at a top end thereof for the egress of the lotion and the active ingredient-containing liquid following their being squeezed from said first and second compartments through said first and second bores into said mixing chamber, said mixing chamber member further having threads formed on an outer surface thereof for removably receiving an internally threaded cap;

(c) means for adjusting the size of said second bore whereby the quantity of said active ingredient and thereby the quality of dispensed quantities of mixtures of said lotion and said active ingredient are adjustable; and (d) indicia means associated with said means for adjusting the size of said second bore for indicating the quality of a mixture associated with sizes of said second bore whereby the quantity of said active ingredient and thereby the quality of dispensed quantities of mixtures of said lotion and said active ingredient is selectable; and wherein, (e) said first bore is concentrically disposed in said neck;

(f) said second bore is peripherally disposed with respect to said first bore; and, (g) said means for adjusting the size of said second bore comprises a selector dial rotatably mounted on said neck, said selector dial having a central cap portion covering said neck over which said mixing chamber member is disposed, said central cap portion having a central bore through a top member thereof concentrically disposed over said first bore and a plurality of various diameter metering bores disposed peripherally through said top member concentrically disposed to pass over said second bore as said selector dial is rotated on said neck.

4. The bottle of claim 3 and additionally comprising: said indicia means being on said selector dial for indicating the quality of a mixture associated with respective ones of said metering bores whereby the quantity of said active ingredient and thereby the quality of dispensed quantities of mixtures of said lotion and said active ingredient is selectable.

5. A bottle for holding, mixing, and dispensing an adjustable SPF mixture of a lotion and a liquid containing a sunscreening agent comprising:

(a) a plastic bottle containing first and second compartments for containing, respectively, the lotion and the sunscreen agent-containing liquid and having a cylindrical neck at the top thereof containing a first bore therethrough communicating with said first compartment and a second bore therethrough communicating with said second compartment, said first bore being concentrically disposed in said neck and sized for passing known quantities of said lotion, said second bore being peripherally disposed with respect to said first bore and sized in relation to said first bore so as to add a quantity of said sunscreen agent which will impart a preselected maximum SPF value to dispensed quantities of mixtures of said lotion and said sunscreen agent;

(b) a selector dial rotatably mounted on said neck, said selector dial having a central cap portion covering said neck, a central bore through a top member thereof concentrically disposed over said first bore, and a plurality of various diameter metering bores disposed peripherally through said top member concentrically disposed to pass over said second bore as said selector dial is rotated on said neck;

(c) indicia means disposed on said selector dial for indicating the SPF value of a mixture associated with respective ones of said metering bores whereby the quantity of said sunscreen agent and thereby the SPF value of dispensed quantities of mixtures of said lotion and said sunscreen agent is selectable; and, (d) a generally cylindrical mixing chamber member disposed over said central cap portion of said selector dial, said mixing chamber member having an internal mixing chamber communicating with said first and second bores and said central and metering bores on a bottom end thereof and having a third bore therethrough at a top end thereof for the egress of the lotion and the sunscreen agent-containing liquid following their being squeezed from said first and second compartments through said first and second bores, said central bore, and one of said metering bores into said mixing chamber; said mixing chamber member further having threads formed on an outer surface thereof for removably receiving an internally threaded cap.

* * * * *